United States Patent
Roudil et al.

(12) 
(10) Patent No.: US 6,560,548 B1
(45) Date of Patent: May 6, 2003

(54) DEVICE AND METHOD FOR DETERMINATION OF PHYSICAL PARAMETERS FOR A TWO-PHASE MIX BY PROPAGATION OF AN ACOUSTIC WAVE IN THE CONTINUOUS PHASE OF THE TWO-PHASE MIX

(75) Inventors: Danièle Roudil, Tresques (FR); Francis Malzieu, Piolewc (FR); Gilles Despaux, Saint Georges d'Orques (FR); Jacques Attal, St. Clément de Riviere (FR); Philippe Combette, Montpellier (FR)

(73) Assignee: Commissariat A l'Energie Atomique, Paris (FR)

(*) Notice: Subject to any disclaimer, the term of this patent is extended or adjusted under 35 U.S.C. 154(b) by 0 days.

(21) Appl. No.: 09/720,725
(22) PCT Filed: Jun. 30, 1999
(86) PCT No.: PCT/FR99/01574
§ 371 (c)(1),
(2), (4) Date: Jan. 24, 2001
(87) PCT Pub. No.: WO00/02040
PCT Pub. Date: Jan. 13, 2000

(30) Foreign Application Priority Data

Jul. 1, 1998 (FR) .............................. 98 08404

(51) Int. Cl.$^7$ .................. G10K 15/00; G01N 29/00; G01B 5/30
(52) U.S. Cl. .............. 702/39; 702/103; 73/584
(58) Field of Search ............... 702/34, 39, 48, 702/103, 72, 79; 73/584, 590; 367/47–50, 123–125

(56) References Cited

U.S. PATENT DOCUMENTS

| | | | |
|---|---|---|---|
| 4,497,208 A | * | 2/1985 | Oja et al. ............... 73/584 |
| 4,726,221 A | | 2/1988 | Tavlarides et al. |
| 5,628,937 A | * | 5/1997 | Oliver et al. ............ 264/9 |

FOREIGN PATENT DOCUMENTS

| | | |
|---|---|---|
| EP | 0671547 | 9/1995 |
| EP | 0671547 A1 * | 9/1995 |
| FR | 2478314 | 9/1981 |
| WO | WO94/04907 | 3/1994 |

* cited by examiner

Primary Examiner—Bryan Bui
(74) Attorney, Agent, or Firm—Thelen Reid & Priest; Robert E. Krebs

(57) ABSTRACT

A device measures the propagation time for an acoustic wave in a continuous phase of a two-phase mix (28) comprising the continuous phase and a dispersed phase forming droplets (40) in the continuous phase. The device comprises an electro-acoustic transducer (12) capable of emitting acoustic waves (30) and outputting a reception signal of reflected acoustic waves, a signal pulse generator capable of determining a propagation time starting from signals output by the transducer, and an acoustic lens for focusing acoustic waves and the frequency of the acoustic waves being adjusted to cause reflection of the waves on the droplets of the dispersed phase, essentially located within a focusing area.

18 Claims, 5 Drawing Sheets

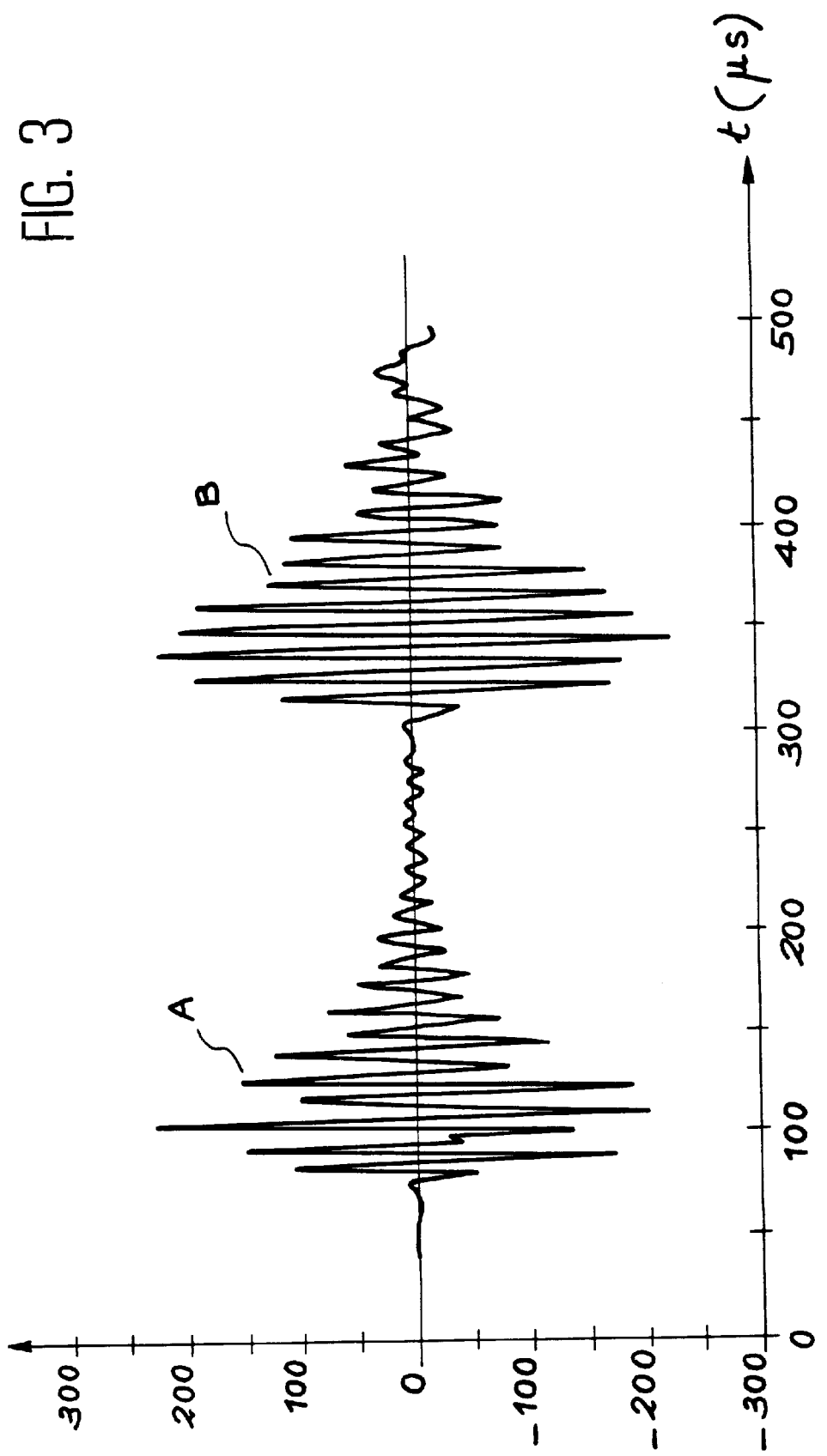

DEVICE AND METHOD FOR DETERMINATION OF PHYSICAL PARAMETERS FOR A TWO-PHASE MIX BY PROPAGATION OF AN ACOUSTIC WAVE IN THE CONTINUOUS PHASE OF THE TWO-PHASE MIX

This application is a national phase of PCT/FR99/01574 which was filed on Jun. 30, 1999 and was not published in English.

TECHNICAL FIELD

This invention relates to a device and a process for determining the physical parameters of a two-phase mix by propagating an acoustic wave in the continuous phase of the mix. For example, the invention can be used to determine the propagation time of an acoustic wave in the continuous phase of the two-phase mix. In particular, the device can be used to measure the acoustic impedance of this phase, its density and the propagation velocity of the acoustic wave in the continuous phase.

For the purposes of the invention, a two-phase mix means any emulsion or dispersion in which a first solution or first phase is in the form of a continuous phase, and a second solid, liquid or gaseous phase is in the form of droplets or particles dispersed in the continuous phase. The second phase is called the dispersed phase.

This type of two-phase mix is used particularly to separate chemical elements in solution. The separation process consists essentially of putting a first solution containing chemical elements into contact with a second solution that acts as an extractor. Putting them into contact in this way enables transfer of material between the two solutions.

The transfer of material is facilitated by the formation of a two-phase mix in the form of an emulsion or dispersion of fine droplets. Settlement finally separates the liquids after the material has been transferred.

Different separation devices operating according to the process mentioned above are known. These include mixer-decanter type devices, centrifugal extractor devices, or pulsed column devices.

The invention may be used to analyze the physical or chemical properties of a two-phase mix, and in particular is used for monitoring parameters essential for such an analysis, namely firstly the propagation velocity of an acoustic wave in the continuous phase of the mix and secondly its density. A change in the propagation velocity is recorded whenever the density of the continuous phase is modified. For example, this type of change in the density corresponds to a transfer of material between the phases.

The invention is used for applications in the oil, pharmaceutical, chemical and food processing industries, in the treatment of radioactive waste and more generally in any field in which an emulsion needs to be characterized.

STATE OF PRIOR ART

When a separation process is used, the two-phase mix is usually monitored, particularly by determining the proportion of each phase in the mix.

Document (1), referenced at the end of the description, describes in particular a process for measurement of the fraction by volume of one of the phases in a two-phase mix consisting of a first phase $F_1$ kept inside a receptacle, in the dispersed state in a second phase $F_2$. According to this process, the propagation velocity $v_1$ of an ultrasound signal in phase $F_1$, and the propagation velocity $v_2$ of an ultrasound signal in phase $F_2$ are determined, and an ultrasound signal is then emitted at a point $P_1$ in the said receptacle, the passage of the said signal at a point $P_2$ in the said receptacle located at distance d from point $P_1$ is detected, the time t spent by the said signal to travel the distance d is determined, and the fraction by volume $\epsilon_1$ of phase $F_1$ and/or the fraction by volume $\epsilon_2$ of phase $F_2$ are calculated using the following equations:

$$\epsilon_1 = \frac{v_1}{d} \cdot \frac{v_2 t - d}{v_2 - v_1} \text{ and}$$

$$\epsilon_2 = \frac{v_2}{d} \cdot \frac{v_1 t - d}{v_1 - v_2}$$

Document (2), also referenced at the end of this description, relates to a similar process also using a method for measuring the propagation time for an acoustic wave in a two-phase mix.

The first step in calculating the fraction by volume of either of the phases, is to determine the propagation velocities $(v_1, v_2)$ of the acoustic wave in each phase, as is the case in document (1).

Thus, document (2) describes how to measure the wave propagation velocity in each of the liquids to be mixed, before making the mix.

One difficulty in measuring the fraction by volume of either of the phases is due to the fact that the propagation velocities or propagation times are not constant during the separation. These parameters are influenced by temperature modifications, but also by changes to the density of the phases related to the material transfer.

It is not very difficult to determine the change in propagation velocities and times as a function of the temperature.

There are two possible methods at the moment of allowing for the change in propagation velocities or times as a function of material exchanges from one phase to the other.

The first method is to take samples of a small volume of emulsion during the separation treatment, and to make acoustic propagation velocity or time measurements separately in each phase after allowing them to settle.

However, there are disadvantages with this first method. Taking the sample of emulsion can disturb operation of the separation device. Furthermore, sampling is only possible if the separation device contains a sufficiently large volume of the mix. Moreover, the sampled volume must be reinjected into the separation device or must be stored after each measurement.

Finally, in the case in which the two-phase mix contains strongly radioactive bodies, it may be impossible to extract and store measurement samples.

A second method of determining the wave propagation velocities or times in each of the phases separately during the treatment is to form settlement chambers in the separation device adjacent to a mixing area. These "in situ" settlement chambers can modify the hydraulic behavior of the device and make local modifications to the characteristics of the two-phase mix.

These devices are also used for on-line measurement of the density of the continuous phase.

DISCLOSURE OF THE INVENTION

The purpose of this invention is to propose a process and a device for determining physical parameters such as the propagation velocity of an acoustic wave in the continuous phase of a two-phase mix, the acoustic impedance of the continuous phase and/or its density, and with none of the difficulties mentioned above.

One purpose in particular is to enable this type of continuous measurements to be taken without interrupting the separation process and without taking any samples of the two-phase mix.

Another purpose is to propose a non-intrusive device and process that have no influence on the hydraulic operation of separation equipment and that do not modify the characteristics of the two-phase mix.

In order to achieve these purposes, the purpose of the invention is more precisely a device for measuring the propagation time of an acoustic wave in a continuous phase of a two phase mix, the device comprising an electro-acoustic transducer capable of emitting acoustic waves and outputting a reflected acoustic wave reception signal, and means of using transducer signals to determine the time necessary for propagation of waves from the signals output by the transducer. The device also comprises means of focusing the acoustic waves in a focusing area and the frequency of the acoustic waves is adjusted to reflect the waves on the droplets of the dispersed phase, located approximately in the focusing area.

The wavelength $\lambda$ of the acoustic wave produced by the electro-acoustic transducer is such that:

$$\lambda = \frac{v_c}{f}$$

In this equation, $V_c$ represents the wave propagation velocity in the continuous phase and f is the wave frequency.

A droplet of the dispersed phase located within the focusing area causes a local disturbance of the acoustic impedance of the medium through which the wave passes at this location. The acoustic impedance of a medium is defined in this case as the product of its density and the wave propagation velocity in the medium.

The acoustic wave may be reflected by a droplet of the dispersed phase present in the focusing area and the energy of the reflected acoustic signal is proportional to the difference between the acoustic impedances of the dispersed phase and the continuous phase. Efficient reflection is obtained when the diameter of the droplets is greater than the wavelength $\lambda$.

Thus, starting from an estimate of the velocity $V_c$, the minimum frequency can be determined as a function of the diameter $\phi$ of the smallest droplets present significantly in the two-phase mix. For example, the frequency is adjusted to fix the wavelength $\lambda$ such that $\lambda = \phi/5$.

The use of an ultrasound transducer operating at a high frequency, for example above 100 MHz, guarantees that reflections will occur on the droplets even if there is a large change in the two-phase mix. The size of the droplets in a separation device changes as a function of the operating conditions and the retention rate of the continuous phase.

The focusing distance of the acoustic wave is preferably chosen as a compromise between the minimum droplet diameter that can be measured for a given frequency and attenuation of the wave in the continuous phase. This means that the propagation time can be determined with a good precision with a reasonable probability of passing through the focusing area of a droplet during a measurement time, taking account of an average distance between the droplets.

For example, the focusing distance may be of the order of one millimeter.

The frequency of the acoustic wave may also be optimized as a function of the attenuation of the medium.

The propagation time in the continuous phase of a wave that is reflected on a droplet located in the focusing area corresponds to the time taken to travel twice the focal distance of the focusing means.

Thus, means for using the signals output by the device according to the invention can be provided to determine the wave propagation velocity Vc in the continuous phase according to the equation $$v_c = \frac{2F}{T}$$

In this equation, F is the focal distance of the focusing means and T is the propagation time.

For example, the focusing means may comprise an acoustic lens with a first face on which the electro-acoustic transducer is fitted, and a second face with at least one concave portion with a radius of curvature R, facing the mix, and called the emission face. This emission face is designed to focus acoustic waves towards the focusing area. When an acoustic wave is emitted, a first partial reflection takes place on the emission face, and then a second series of reflections may also take place on a droplet inside the focusing area.

Thus, according to one particular aspect of the invention, the means of using the signals may be designed to set up a delay time between a first reflection signal on the emission face of the lens and a second reflection signal on a droplet of the dispersed phase, in response to the same emitted acoustic wave. The propagation time for the wave that travels twice the focal distance F of the lens is then equal to this delay time.

The propagation velocity of the acoustic wave can then be calculated from the focal distance F according to the equation $$v_c = \frac{2F}{T}$$

indicated above, or as a paraxial approximation starting from the radius of curvature R of the emission face and the propagation velocity $V_v$ in the lens material.

The result is $$F = \frac{R}{1 - V_c/V_v} = \frac{V_c \cdot T}{2}$$

Thus, $V_c^2 - V_c \cdot V_v + 2 \cdot R \cdot V_v / T = 0$.

$V_c$ can be calculated from this equation (in glass, $V_v \approx 5968$ m.s$^{-1}$).

The amplitude of the signal output by the transducer is greater when the acoustic impedance of the droplet is not the same as the acoustic impedance of the liquid forming the continuous phase. As a first approximation, it is assumed that the droplet can be represented by a plane disk that passes in front of the focusing area. It is assumed that the dimension of the droplet is greater than the acoustic wavelength. In the most favorable case, the collected signal can be modeled by the function $$V(z) = \int_0^{\theta_0} R(\theta)P(\theta)\cos\theta e^{kz\cos\theta} d\theta$$

in which V(z) represents the output signal when the droplet moves along an axis of the acoustic lens by a distance z, $R(\theta)$ is the reflection power of the droplet, $\theta$ is the angle of incidence at which the acoustic wave reaches the droplet, $P(\theta)$ is a function corresponding to the opening of the lens (pupil function), k is the wave vector in the continuous medium and $\theta_0$ is the half-opening angle of the lens ($\approx 50°$). The maximum signal amplitude is obtained when the droplet is in or close to the focal plane. This characteristic can be used to accurately determine the flight time T between the emission face of the lens and the focusing area. The propagation time is preferably determined based on a large number of passes through droplets near the focal point.

According to one particular embodiment of the acoustic lens, its emission face may comprise at least one concave portion capable of focusing acoustic waves, and a plane portion capable of reflecting non-focused waves.

It is not essential to make the emission face with a plane part, but it does make it possible to make measurements of reflections of waves riot focused on this part more accurately. This point is described in more detail in the rest of the text.

According to one improvement, the emission face of the acoustic lens may also be covered with a thin coat of anti-reflection material with a thickness approximately equal to $\lambda_0/4$, where $\lambda_0$ is the acoustic wavelength. Furthermore, the acoustic impedance $Z_a$ of the coat of anti-reflection material may also be chosen equal to $Z_a = \sqrt{Z_L . Z_C}$, where $Z_L$ is the acoustic impedance of the material (for example glass) from which the acoustic lens is made, and $Z_C$ is the estimated impedance of the continuous phase.

The anti-reflection coating performs two functions, firstly it improves the determination of a reflection power of the continuous phase (described later) by the plane portion of the emission face, and secondly it corrects convergence astigmatism of the concave part of the emission face.

Note that the use of an acoustic lens is not the only possible means of focusing the acoustic wave. Thus, as a variant, the transducer may be a segmented type transducer comprising a plurality of transducer elements (sensors) that can be excited separately. These elements, individually controlled by adapted electronic circuits, are used to directly focus the acoustic wave produced. They can thus form focusing means according to the meaning of the invention.

According to one particular application of the invention, the process can be used to measure the propagation velocity of an acoustic wave in the continuous phase of a two-phase mix comprising the continuous phase and a dispersed phase forming droplets in the continuous phase. According to this process:
  acoustic waves focused in a focusing area are emitted in the continuous phase, the frequency of the acoustic wave being adjusted to enable a reflection on droplets in the dispersed phase located approximately in the focusing area,
  the first reflection signals from waves on the droplets are recorded,
  a propagation time for the wave is determined from the reflection signals, and
  the propagation velocity is calculated starting from the propagation time and an acoustic wave focusing distance.

According to another particular application of the invention, the reflection signals may also be used to determine the reflection power of the continuous phase. This reflection power is defined as the ratio of the amplitude of the reflected signals to the amplitude of the emitted acoustic signals.

In this respect, the second reflection signals from an acoustic wave reflected at an interface between the acoustic lens of the electro-acoustic transducer and the continuous phase, can be recorded.

Preferably, reflection signals from the plane portion of the emission face corresponding to a non-focused wave can be used to determine the reflection power $R_c$.

For example, the signal amplitude can be recorded and measured using a simple oscilloscope.

The reflection power Rc of the continuous phase can be determined directly from the signal amplitude, for example as a function of a predetermined (approximately linear) calibration curve.

The calibration curve may be determined by dipping the lens in the fluids for which the reflection power is known, for example such as air or water, and measuring the amplitude of the waves reflected by these fluids.

According to another possibility, the reflection power of the continuous phase may be determined as the ratio of the amplitude of signals reflected from the continuous phase, to the amplitude of the emitted signals.

The amplitude and therefore the energy of the emitted signals may be known starting from an additional and partial reflection of the signals on a reference diopter. This aspect will be dealt with in more detail in the rest of the description.

According to another aspect of the invention, it is also possible to establish an acoustic impedance $Z_c$ of the continuous phase, if the reflection power $R_c$ of the continuous phase is known, by using the following equation:

$$Z_C = Z_L \frac{1 - R_C}{1 + R_C},$$

where $Z_L$ is an acoustic impedance (known) of the material from which the acoustic lens is made.

When an anti-reflection coat with acoustic impedance $Z_a$ is provided on the acoustic lens, the result is $$Z_C^2 = Z_L \cdot Z_a \cdot \frac{1 - R_C}{1 + R_C}$$

According to another aspect of the invention, the density ρc of the continuous phase can also be established from the following equation:

$$\rho c = \frac{Z_C}{V_C}$$

The reflection power $R_D$ between the continuous phase and the dispersed phase can also be determined from a measurement of the maximum amplitude of the said first reflection signals, in other words signals corresponding to a reflection on the droplets of the dispersed phase.

In this case, the value of $R_D$ is also obtained by comparing the amplitude of the first reflection signals with a predetermined calibration curve, using dispersions or media with known properties.

Finally, knowing the acoustic impedance of the continuous phase and the reflection power $R_D$, the acoustic impedance $Z_D$ of the dispersed phase can be calculated using the following equation:

$$Z_D = Z_C \frac{1 - R_D}{1 + R_D}$$

In this equation, Zc is the impedance of the continuous phase determined in advance as described above.

Other characteristics and advantages of this invention will become clearer from the following description given with reference to the figures in the attached drawings. This description is given for illustrative purposes only and is in no way limitative.

BRIEF DESCRIPTION OF THE FIGURES

FIG. 3 shows a record of reflection signals on a droplet and on a front face of the lens, output by the transducer on FIG. 2.

DETAILED DESCRIPTION OF EMBODIMENTS OF THE INVENTION

For simplification reasons, identical, similar or equivalent elements on the different figures are assigned the same references in the following description.

Figure 1:
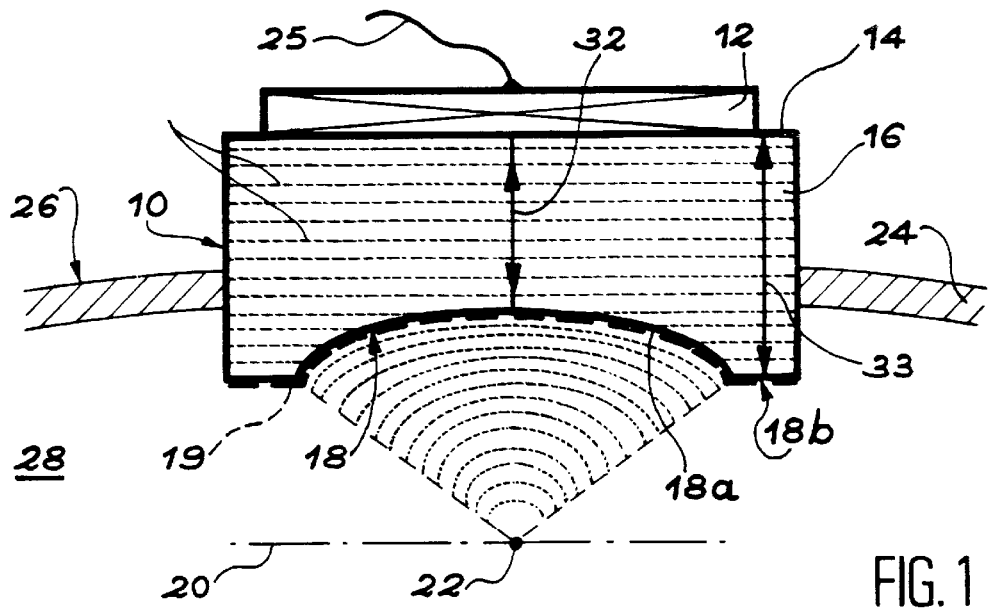
FIG. 1 is a diagrammatic view through an electro-acoustic transducer with an acoustic lens, the transducer being useable in a device according to the invention.

Reference 10 on FIG. 1 generally denotes an electro-acoustic transducer that can be fitted on a device according to the invention.

The transducer 10 comprises an electro-acoustic transducer 12, for example such as a piezoelectric device, fixed on a first face called the back face 14 of a delay line 16.

For example, the delay line could be a cylindrical block made of a material that does not absorb acoustic waves, such as glass. It has a second face called an emission face 18, in which there is a concave portion 18a with a radius of curvature R, designed to focus acoustic waves and a portion 18b that is plane. The delay line thus forms an acoustic lens. The delay line is referred to as an "acoustic lens" in the rest of this text. An anti-reflection coating 19 made of a material such as Teflon or silicone covers the emission face 18 of the acoustic lens.

A chain dotted line 20 shows a focal plane passing through the focal point 22 of the acoustic lens 16. For example, the focal distance measured between the emission face 18 and the focal point could be 1 mm.

The acoustic transducer 10 may for example be housed in the wall 24 of a separation device 26 such that the emission face 18 of the acoustic lens 16 faces towards the inside of the separation device that contains a two-phase mix 28.

For example, the two-phase mix 28 may contain a continuous phase of $HNO_3$, in which a dispersed phase of TBP (tributyl phosphate) is mixed with 30% of dodecane in the form of droplets.

In other applications, the dispersed phase may also comprise solid particles or gas bubbles.

The electro-acoustic transducer 12 is connected by wires 25 to external electrical devices not shown on FIG. 1, that can be used to apply an excitation signal to the transducer and to measure one or several reception signals on the transducer.

When an electric excitation signal is applied to the piezoelectric device 12, this device emits an acoustic wave diagrammatically represented as reference 30.

The acoustic wave propagates through the lens to be focused on focal point 22. Furthermore, as shown by the two double arrows 32 and 33, part of the wave is reflected on the emission face 18 of the lens 16 and returns to the transducer.

However, the part of the wave transmitted in the two-phase mix 28 is not reflected.

The piezoelectric device 12 operates according to a sequence of emission and reception phases.

During an emission phase with a duration for example of the order of 30 ns, the transducer emits a wave in response to an excitation signal, preferably a pulse signal. For example, the signal frequency may be 100 MHz.

During a reception phase with a duration for example of the order of 150 ns, the transducer outputs a reception signal corresponding to the reflected waves that it detects.

Figure 2:
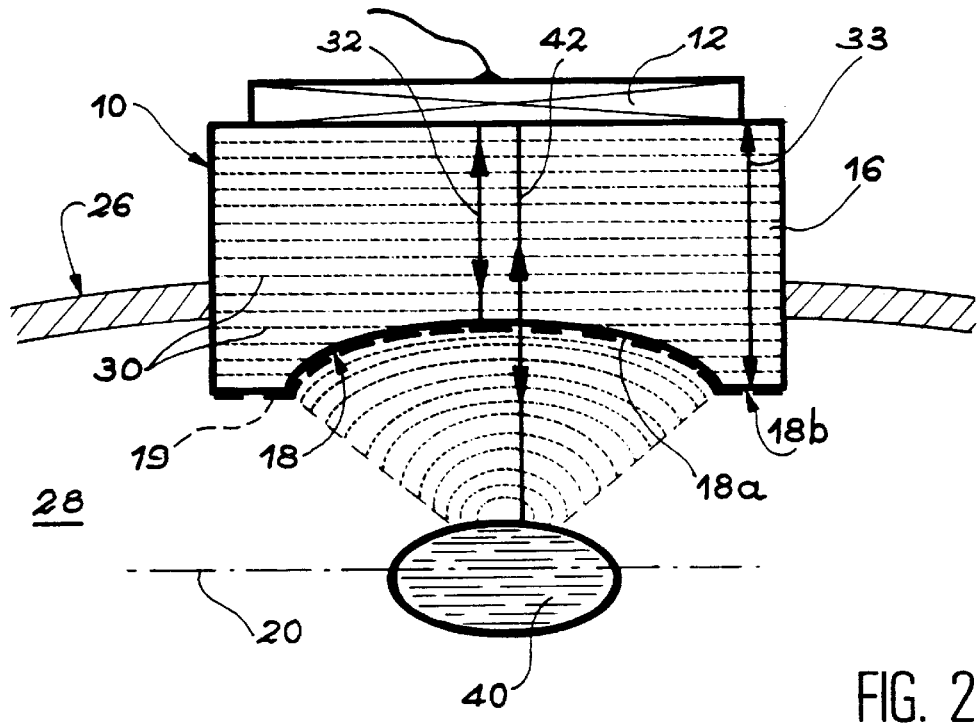
FIG. 2 shows the sensor on FIG. 1 in the presence of a droplet in a focusing area of the lens.

FIG. 2 shows sensor 10 on FIG. 1 in a situation in which a droplet 40 is located in a focusing area, in other words approximately at the focal point.

The acoustic wave emitted by the piezoelectric device is then reflected not only by the emission face 18 of the lens 16 as shown by the double arrows 32 and 33, but also by the droplet 40.

FIG. 2 shows a double arrow 42 denoting the wave emitted by the transducer that is focused on the droplet 40, and a reflected wave or echo originating from droplet 40.

FIG. 3 shows records of signals corresponding to waves reflected on the front face of the acoustic lens in a simplified manner, and partly on the plane portion of this face and on a droplet of the dispersed phase. FIG. 3 shows the amplitude of the signals as the ordinate, at an arbitrary scale. The time (in $\mu s$) is shown on the abscissa.

Reference A on FIG. 3 denotes a first signal corresponding to reflection on the concave portion of the front face of the lens.

Reference B on FIG. 3 denotes a second signal corresponding to reflection on the plane portion of the front face of the lens.

The maximum amplitude of the signals A and B is a means of directly establishing the reflection power $R_c$ of the continuous phase at a lens/continuous phase interface.

Similarly, the measurement of the maximum amplitude of reflection signals on a dispersion droplet (not visible on FIG. 3), in other words at a continuous phase/dispersion interface, can be used to establish the reflection power of the dispersion at this interface.

The relation between the maximum amplitude of signals and the reflection powers depends mainly on the gain of the measurement instruments such as the oscilloscope, and can be determined starting from material samples for which the reflection power is known.

As mentioned above, knowledge of the reflection powers is a means of calculating the acoustic impedances of the phases.

The density of the continuous phase can then be determined knowing these impedances and the propagation velocity of the acoustic wave in the continuous phase.

Figure 4:
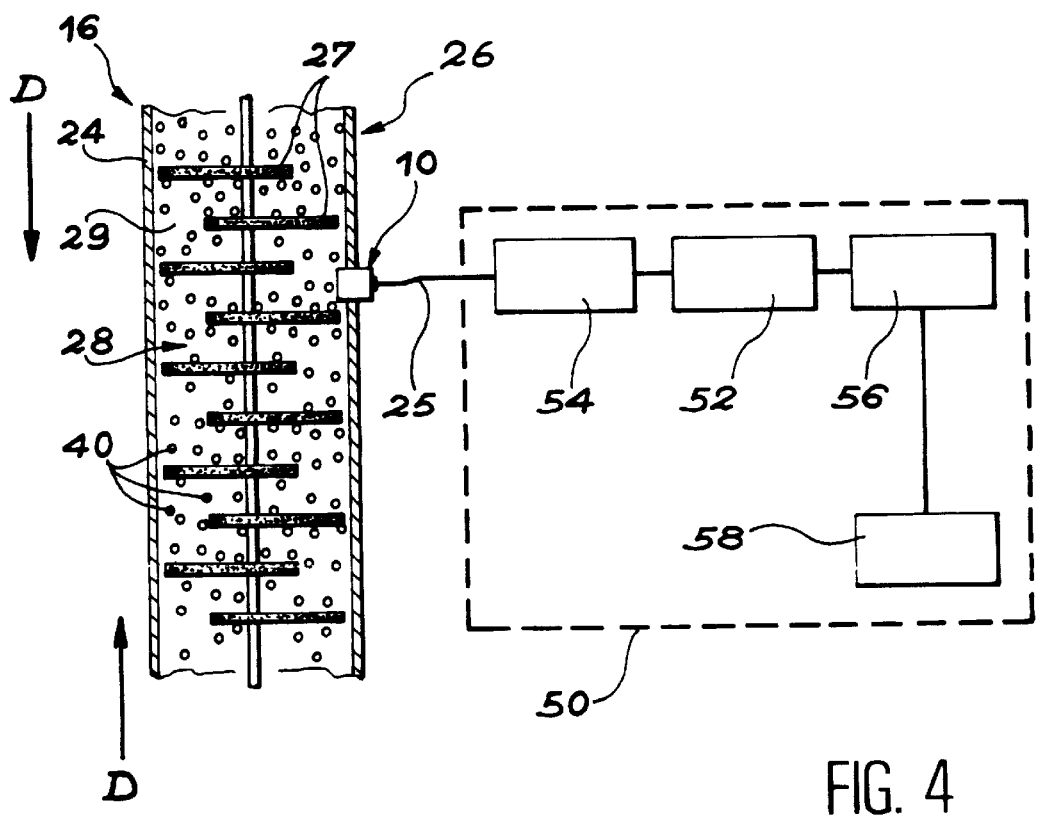
FIG. 4 shows a segment of a pulsed column equipped with a device according to the invention.

FIG. 4 described below shows one possible use of the device according to the invention.

On this figure, reference 26 denotes a segment of a pulsed column with perforated mixing trays 27, in which two liquid phases are put into circulation in opposite directions to form a two-phase mix 28. The mix contains a continuous phase 29 in which droplets 40 of a dispersed phase move. The direction of displacement of the droplets 40 is identified by an arrow D.

A transducer 10 like that described with reference to the previous figures is formed in the wall 24 of the pulsed column and is connected through wires 25 to a signal pulse generation and usage line 50.

The line 50 comprises an ultrasound generator 52 capable of outputting high frequency electrical pulses to the piezoelectric device in the transducer 10. The ultrasound generator may be connected to the sensor through an impedance matching circuit 54 if necessary.

The echo reception signals output by the piezoelectric device are also directed through the impedance matching circuit 54 to an oscilloscope 56 and to calculation means 58. The oscilloscope 56 displays signals. The calculation means 58, for example a computer, are used to calculate the propagation velocity of the waves in the continuous phase at any time.

Figure 5:
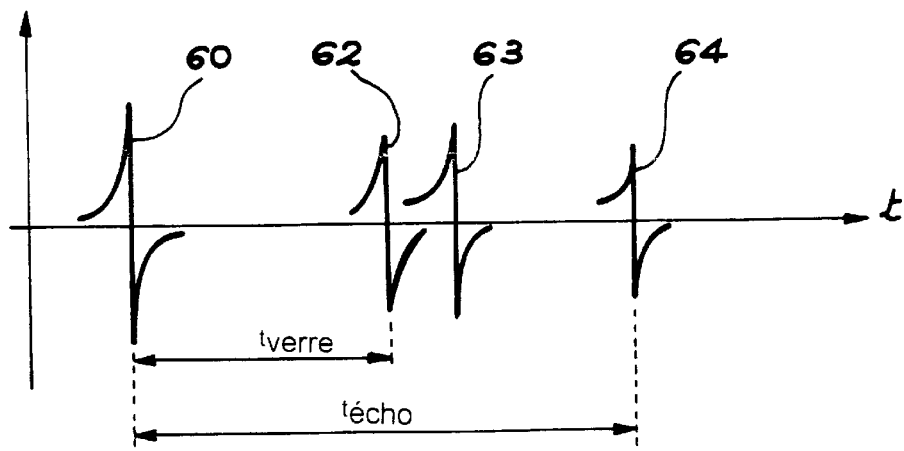
FIG. 5 is a graph showing the variation with time of signals output by the transducer in a device according to the invention.

FIG. 5 is a simplified diagrammatic graph that should be read with FIG. 4 showing examples of signals that could be recorded with the device on FIG. 4.

The scales on FIG. 5 are arbitrary.

Reference 60 indicates a pulse corresponding to the emission of a wave by the piezoelectric device.

References 62 and 63 indicate first and second echoes corresponding to partial reflection of the wave emitted on the plane and convex portions of the lens emission surface, respectively.

Reference 64 indicates a third echo with a maximum amplitude corresponding to a reflection of the wave on a droplet.

As already mentioned, the amplitude of echo 62 contains information about the reflection power of the continuous phase with respect to the glass. Similarly, the amplitude of the echo 64 contains information about the reflection power between the two phases.

A duration indicated by $t_{glass}$ between the pulse 60 and the first echo 62 corresponds to the time taken by the wave to make a forward—return path from the piezoelectric device to the lens emission face.

A duration indicated by $t_{echo}$ corresponds to the time taken by the wave to make a forward—return path from the piezoelectric device to the droplet located at the focal point.

Initially, the wave propagation time in the continuous phase can be determined by subtracting a predetermined fixed quantity corresponding to the time taken by the wave to pass through the focusing means (lens), from the duration $t_{echo}$.

In order to be unaffected by propagation variations in the lens, the propagation time T is preferably measured between the second echo 63 and the third echo 64.

This gives $T=t_{echo}-t_{glass}$.

The propagation time and the propagation velocity can be calculated considering only a small number of measurements (emission-reception of a wave).

However, the precision of the result is improved by carrying out a statistical calculation on a large number of measurements.

For example, it is possible to record successive echoes obtained starting from the emission of 500 000 acoustic pulses.

From these measurements, an average time $t_{echo}$ can be calculated corresponding to the record of maximum amplitude echoes.

With this type of statistical processing, the relative precision of the measurement of the propagation time and the calculation of the propagation velocity can be better than 0.5%.

Figure 6:
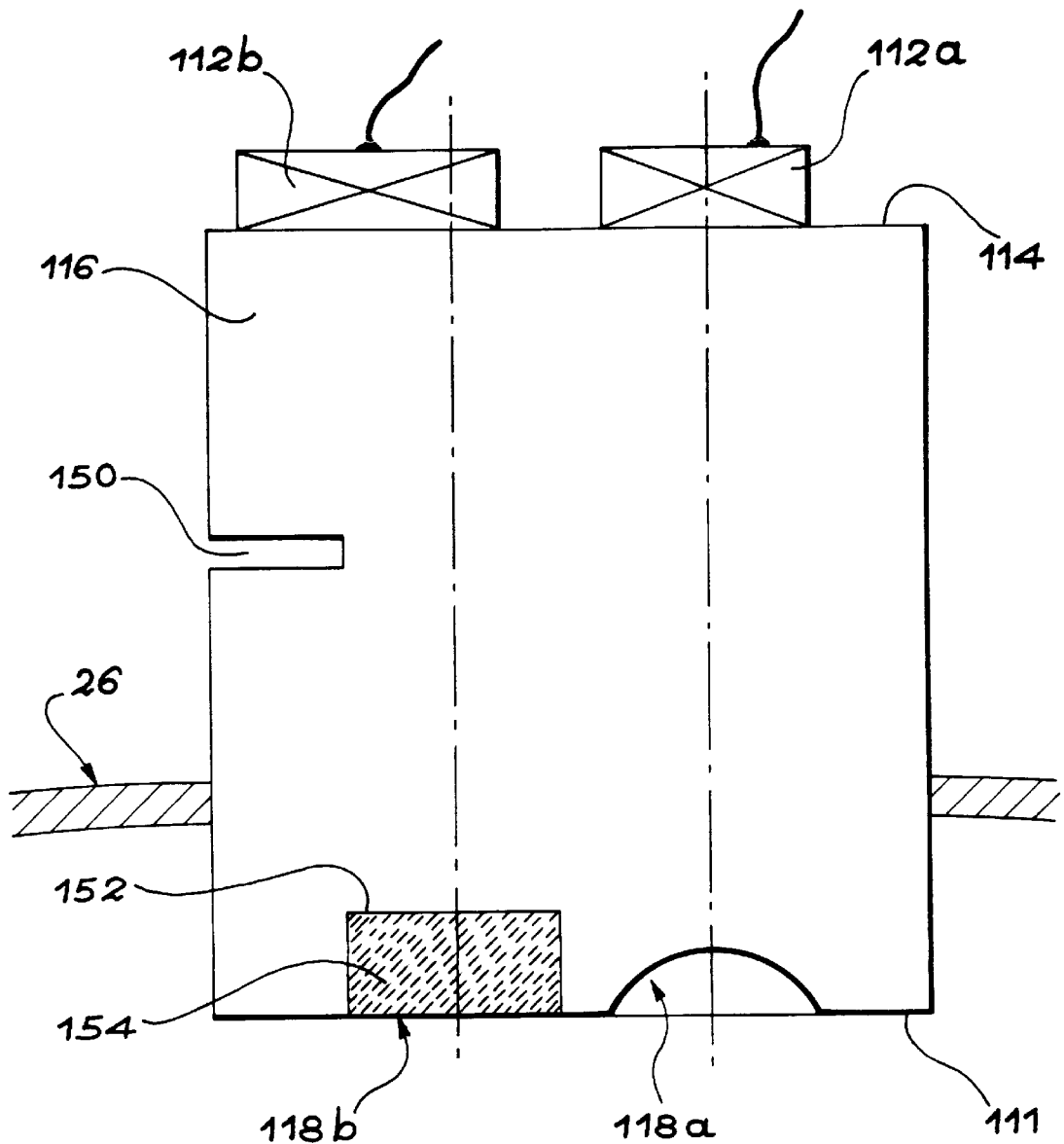
FIG. 6 is a diagrammatic section through an acoustic transducer that can be used in a device according to the invention and forming a variant to the transducer shown on FIG. 1.

FIG. 6 shows a sophisticated acoustic transducer that can be used in the measurement device according to the invention. This device comprises an acoustic lens 116 with a front face 111 that will be put into contact with the two-phase mix for which the characteristics are to be measured. The lens 116 has characteristics comparable with the characteristics of the lens 16 described with reference to FIG. 1.

The front face 111 has a first concave part 118*a* that can focus acoustic waves in the two-phase mix. This concave part is comparable with the concave part 18*a* on FIGS. 1 and 2.

A second part of the front face 111, denoted as reference 118*b*, is a plane part corresponding to part 18*b* on FIGS. 1 and 2.

The back face 114 of the acoustic lens is equipped with two piezoelectric devices 112*a*, 112*b*, associated with a first and second parts 118*a* and 118*b* on the front face. The piezoelectric devices are designed to emit signal waves and to detect reflected waves or echoes. Each assembly formed by a piezoelectric device and a corresponding part of the front face is denoted as a "channel" of the acoustic transducer in the remainder of the text. The channels are independent.

It is observed that the first piezoelectric device 112*a* is aligned with the first part 118*a* of the front face along an axis perpendicular to the front face.

The second piezoelectric device 112*b* is slightly offset from the centerline of the plane part 118*b* so that it is also facing a slit 150 formed in the body of the acoustic lens 116 from one of its lateral sides.

The slit 150 forms a reference diopter such as, for example, a glass—air diopter when the lens is made of glass. The function of the diopter is explained in more detail in the remainder of the text.

Finally, a cavity 152 can be seen formed in the front face 111 of the acoustic lens. The cavity is filled with an impedance matching material 154, for example a vinyl-ester type resin. The free surface of the material is plane and flush with the front face 111. The free surface of the material forms the second part 118*b* (plane) of the front face, in the illustrated example.

The impedance matching material is chosen to have an acoustic impedance as close as possible to the estimated acoustic impedance of the mix to be measured. It is also chosen to have good bond and good resistance to aggression by the media with which it comes into contact.

The front face of the acoustic lens may also be covered with an anti-reflection layer made of a material with an impedance $Z_a$ such that $Z_a = \sqrt{Z_L \cdot Z_C}$. The above description gives more information about this subject.

Due to its two channels, the transducer is capable of separately measuring firstly the reflection power of the continuous phase, and secondly its density or the propagation velocity of a wave in it, under optimum conditions.

The first channel, corresponding to the concave part of the front face, is used to establish a wave propagation time and velocity in the continuous phase. On the other hand, the second channel corresponding to a plane part of the front face, is used to measure the reflection power and therefore the acoustic impedance of the continuous medium.

Figure 7A:
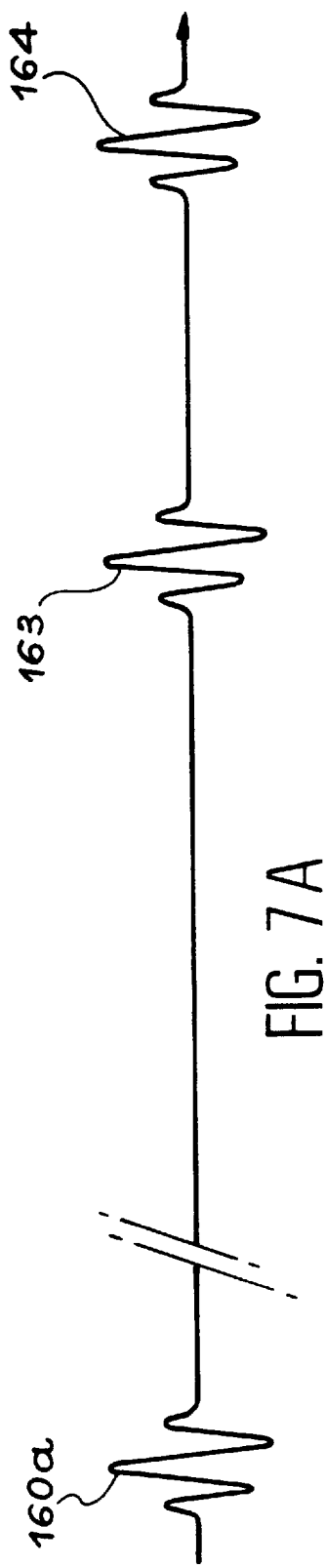
FIG. 7A is a simplified diagrammatic view of signals received by a first channel of the transducer on FIG. 6.

FIG. 7A very diagrammatically shows echoes recorded by the first piezoelectric device 112a of the first channel in response to a signal wave 160a emitted by this device.

A first echo 163 corresponds to the reflection of the wave at the front face 111 of the acoustic lens 116, and a second echo 164 corresponds to reflection (if any) of the wave on a droplet in suspension in the continuous phase.

The echoes are used as described previously with relation to FIGS. 1 to 5.

Figure 7B:
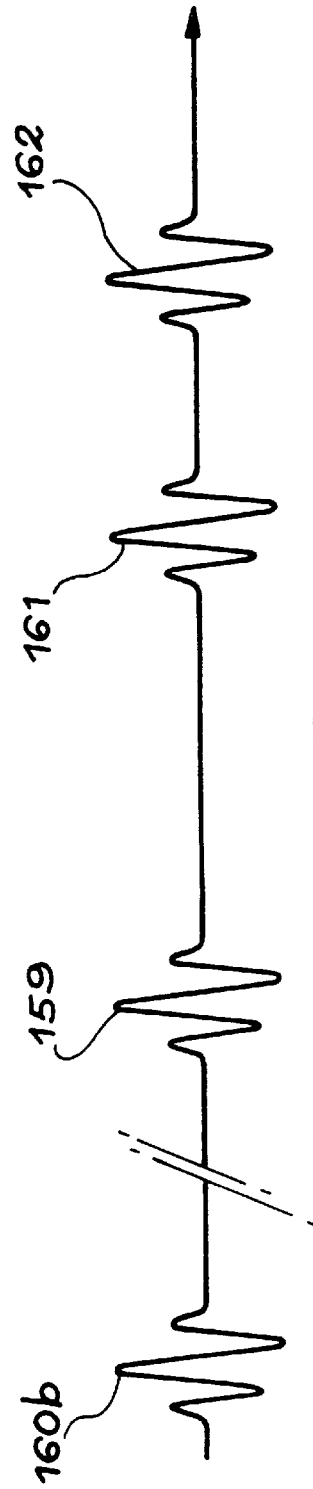
FIG. 7B is a simplified diagrammatic view of signals received by a second channel of the transducer on FIG. 6.

FIG. 7B also diagrammatically shows echoes recorded by the second piezoelectric device 112b of the second channel in response to a wave 160b emitted by this device.

A first reference echo 159 corresponds to a part of the wave that is subjected to an almost total reflection, or at least a known reflection, on the reference diopter formed by the slit 150.

A second echo 161 corresponds to a reflection at the glass-resin interface, in other words at the interface between the body of the acoustic lens and the impedance matching material.

A third echo 162 corresponds to a reflection of the emitted wave at the resin-continuous phase interface, in other words between the impedance matching material flush with the front face of the lens and the continuous phase.

The reference echo is used to know the energy or the amplitude of the signal wave initially emitted by the piezoelectric device.

The reflection properties of the reference diopter are known, consequently the amplitude of the reference echo is proportional to the amplitude of the initially emitted wave. When reflection on the reference diopter is total, the amplitude of the reference echo is equal to the amplitude of the emitted wave and can be used directly to determine the reflection power $R_C$ of the continuous phase.

The reflection power $R_c$ is equal to the ratio of the amplitude of the reflected wave, in other words the wave corresponding to the third echo 162 to the amplitude of the emitted wave.

For simplification reasons, the waves shown on FIGS. 7A and 7B ignore the reflection powers of the media and are all shown with an identical amplitude.

Preferably, the two channels of the acoustic transducer are not activated simultaneously. A first series of measurements may be made initially using the second channel in order to determine the acoustic impedance of the continuous phase. The second channel can be used in a second step to determine the propagation velocity and the density of the continuous phase.

Referenced Documents (1)

FR-A-2 478 314

(2)

U.S. Pat. No. 4,726,211

What is claimed is:

1. Device for measuring the propagation time of an acoustic wave in a continuous phase of a two-phase mix (28) comprising the continuous phase and a dispersed phase forming droplets (40) in the continuous phase, the device comprising:

an electro-acoustic transducer (12) capable of emitting acoustic waves (30) and outputting a reception signal of reflected acoustic waves;

means for using the transducer signals to determine a propagation time starting from signals output by the transducer; and means for focusing the acoustic waves into a focusing area and the frequency of the acoustic waves being adjusted to cause reflection of the waves on droplets of the dispersed phase, substantially located within the focusing area.

2. Device according to claim 1, in which the focusing means comprise an acoustic lens (16) with an emission face (18).

3. Device according to claim 2, in which the emission face (18, 111) of the acoustic lens comprises at least a concave portion (18a, 118a) capable of focusing the acoustic waves and a plane portion (18b, 118b) capable of reflecting the non-focused waves.

4. Device according to claim 3, in which the acoustic lens comprises a first piezoelectric element (112a) associated with the concave part (118a) of the emission face, and a second piezoelectric element (112b) associated with the plane part (118b) of the emission face.

5. Device according to claim 4, in which the lens also comprises a reference diopter (150) associated with the second piezoelectric element (118b).

6. Device according to claim 3, in which the acoustic lens comprises a region made of an impedance matching material (154) with a free, plane surface flush with the plane part of the emission face.

7. Device according to claim 6, in which the impedance matching material fits into a cavity (152) formed in the acoustic lens from the emission face.

8. Device according to claim 2, in which the emission face comprises an anti-reflection coating.

9. Device according to claim 2, in which means for using the transducer signals are capable of setting up a delay time between a first reflection signal (62) on the emission face of the lens and a second reflection signal (64) on a droplet of the dispersed phase in response to the same emitted acoustic wave.

10. Device according to claim 2, in which the means for using the signals comprise means for measuring an amplitude of a signal reflected on at least one portion of the emission face of the acoustic lens to determine a reflection power $R_c$ of the continuous medium.

11. Device according to claim 1, in which the means for using the signals are also capable of determining an acoustic propagation velocity $V_c$ in the continuous phase using the equation:

$$v_c = \frac{2F}{T}$$

where F is a focal distance of the focusing means and T is the wave propagation time.

12. Device according to claim 1, in which the means for using the signals also comprise means for measuring an amplitude of a signal reflected on a droplet of the dispersed phase in order to determine a reflection power between the continuous phase and the dispersed phase.

13. Process for determining propagation parameters of an acoustic wave in the continuous phase a two-phase mix (28) comprising the continuous phase and a dispersed phase forming droplets (40) in the continuous phase, the process comprising:

acoustic waves (30) focused in a focusing area are emitted in the continuous phase, the frequency of the acoustic wave being adjusted to enable a reflection on droplets of the dispersed phase, located approximately in the focusing area, first reflection signals of the waves on the droplets are recorded, a propagation time of the wave is determined from the reflection signals, and the propagation velocity is calculated from the propagation time and an acoustic wave focusing distance.

14. Process according to claim 13, in which second reflection signals of an acoustic wave reflected at an interface between an acoustic lens of an electro-acoustic transducer and the continuous phase are recorded, and a reflection power $R_c$ of the continuous medium is also determined from a measurement of the amplitude of the said second signals.

15. Process according to claim 14, in which an acoustic impedance $Z_c$ of the continuous phase is also determined, using the following equation:

$$Z_C = Z_L \frac{1 - R_C}{1 + R_C},$$

where $Z_L$ is an acoustic impedance (known) of the material from which the acoustic lens is made.

16. Process according to claim 15, in which a density ρc of the continuous phase is also determined from the acoustic impedance $Z_c$ and the acoustic propagation velocity of the wave in the continuous phase using the following equation:

$$\rho c = \frac{Z_C}{V_C}$$

17. Process according to claim 15 in which a refection power $R_D$ between the continuous phase and the dispersed phase is determined from a measurement of the amplitude of said first reflection signals and an acoustic impedance $Z_D$ of the dispersed phase is further calculated using the following equation:

$$Z_D = Z_C \frac{1 - R_D}{1 + R_D}$$

18. Process according to claim 13, in which a reflection power $R_D$ between the continuous phase and the dispersed phase is determined from a measurement of the amplitude of said first reflection signals.

* * * * *